United States Patent
Terui et al.

(10) Patent No.: US 10,197,684 B2
(45) Date of Patent: Feb. 5, 2019

(54) RADIATION IMAGING APPARATUS, CONTROL METHOD THEREOF, AND NON-TRANSITORY COMPUTER-READABLE STORAGE MEDIUM

(71) Applicant: CANON KABUSHIKI KAISHA, Tokyo (JP)

(72) Inventors: Kosuke Terui, Yokohama (JP); Shinichi Takeda, Kawasaki (JP); Katsuro Takenaka, Honjo (JP); Sho Sato, Tokyo (JP); Atsushi Iwashita, Tokyo (JP); Yoshiaki Ishii, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/564,946

(22) PCT Filed: Jun. 17, 2016

(86) PCT No.: PCT/JP2016/002934
§ 371 (c)(1),
(2) Date: Oct. 6, 2017

(87) PCT Pub. No.: WO2017/010045
PCT Pub. Date: Jan. 19, 2017

(65) Prior Publication Data
US 2018/0136343 A1   May 17, 2018

(30) Foreign Application Priority Data

Jul. 10, 2015 (JP) .................................. 2015-139104

(51) Int. Cl.
*G01T 1/20* (2006.01)
*A61B 6/00* (2006.01)
(Continued)

(52) U.S. Cl.
CPC .......... *G01T 1/2018* (2013.01); *A61B 6/4225* (2013.01); *A61B 6/4233* (2013.01);
(Continued)

(58) Field of Classification Search
CPC ... A61B 6/4225; A61B 6/4233; A61B 6/4241; G01T 1/2018; H04N 5/32; H04N 5/363; H04N 5/374; H04N 5/378
See application file for complete search history.

(56) References Cited

U.S. PATENT DOCUMENTS 7,256,404 B2   8/2007   Inoue et al.
7,342,221 B2   3/2008   Takenaka et al.
(Continued)

FOREIGN PATENT DOCUMENTS

JP   A H05-203754    8/1993
JP   A 2003-279411   10/2003
(Continued)

OTHER PUBLICATIONS

U.S. Appl. No. 15/563,148, filed Sep. 29, 2017, Kosuke Terui.
U.S. Appl. No. 15/791,566, filed Oct. 24, 2017, Atsushi Iwashita.

*Primary Examiner* — Mark R Gaworecki
(74) *Attorney, Agent, or Firm* — Venable LLP

(57) ABSTRACT

A radiation imaging apparatus is provided. The apparatus comprises a scintillator configured to convert radiation into light, a sensor panel in which a plurality of pixels each comprising a light detector configured to detect the light is arranged in a two-dimensional array, and a processing unit. The processing unit comprises a signal generating unit configured to output signals indicating intensities of the light detected by the light detector of each of the plurality of pixels, and a detection unit configured to identify a group of pixels each of which outputs a signal of a level exceeding a reference value out of the signals and detect, based on a
(Continued)

pattern of the group, pileup in which a plurality of radiation photons is detected as a single radiation photon.

19 Claims, 10 Drawing Sheets

(51) Int. Cl.
  *H04N 5/378* (2011.01)
  *H04N 5/32* (2006.01)
  *H04N 5/374* (2011.01)
  *H04N 5/363* (2011.01)
(52) U.S. Cl.
  CPC ............ *A61B 6/4241* (2013.01); *H04N 5/32* (2013.01); *H04N 5/374* (2013.01); *H04N 5/378* (2013.01); *H04N 5/363* (2013.01)

(56) References Cited

U.S. PATENT DOCUMENTS

| | | |
|---|---|---|
| 7,343,000 B2 | 3/2008 | Kameshima et al. |
| 7,381,963 B2 | 6/2008 | Endo et al. |
| 7,386,089 B2 | 6/2008 | Endo et al. |
| 7,391,029 B2 | 6/2008 | Takeda et al. |
| 7,403,594 B2 | 7/2008 | Endo et al. |
| 7,442,939 B2 | 10/2008 | Yagi et al. |
| 7,514,663 B2 | 4/2009 | Yagi et al. |
| 7,514,686 B2 | 4/2009 | Ogawa et al. |
| 7,532,706 B2 | 5/2009 | Kameshima et al. |
| 7,541,591 B2 | 6/2009 | Endo et al. |
| 7,573,038 B2 | 8/2009 | Yokoyama et al. |
| 7,573,041 B2 | 8/2009 | Kameshima et al. |
| 7,595,493 B2 | 9/2009 | Okada et al. |
| 7,613,277 B2 | 11/2009 | Takenaka et al. |
| 7,683,337 B2 | 3/2010 | Takenaka et al. |
| 7,714,294 B2 | 5/2010 | Sawada et al. |
| 7,718,973 B2 | 5/2010 | Endo et al. |
| 7,723,693 B2 | 5/2010 | Okada et al. |
| 7,724,874 B2 | 5/2010 | Kameshima et al. |
| 7,732,776 B2 | 6/2010 | Takenaka et al. |
| 7,750,309 B2 | 7/2010 | Endo et al. |
| 7,777,167 B2 | 8/2010 | Takeda et al. |
| 7,791,035 B2 | 9/2010 | Yokoyama et al. |
| 7,847,263 B2 | 12/2010 | Yagi et al. |
| 7,850,367 B2 | 12/2010 | Takenaka et al. |
| 7,869,568 B2 | 1/2011 | Yokoyama et al. |
| 7,872,218 B2 | 1/2011 | Endo et al. |
| 7,880,145 B2 | 2/2011 | Yagi et al. |
| 7,952,058 B2 | 5/2011 | Nomura et al. |
| 8,093,562 B2 | 1/2012 | Yokoyama et al. |
| 8,107,588 B2 | 1/2012 | Kameshima et al. |
| 8,115,177 B2 | 2/2012 | Takeda et al. |
| 8,222,611 B2 | 7/2012 | Yagi et al. |
| 8,247,779 B2 | 8/2012 | Kameshima et al. |
| 8,304,735 B2 | 11/2012 | Inoue et al. |
| 8,440,975 B2 | 5/2013 | Inoue et al. |
| 8,576,294 B2 | 11/2013 | Kameshima et al. |
| 8,653,463 B2 | 2/2014 | Sawada et al. |
| 8,723,996 B2 | 5/2014 | Yokoyama et al. |
| 8,792,024 B2 | 7/2014 | Takenaka et al. |
| 8,809,795 B2 | 8/2014 | Takenaka et al. |
| 8,829,438 B2 | 9/2014 | Sato et al. |
| 9,048,154 B2 | 6/2015 | Takenaka et al. |
| 9,081,104 B2 | 7/2015 | Sawada et al. |
| 9,128,196 B2 | 9/2015 | Sato et al. |
| 9,134,432 B2 | 9/2015 | Iwashita et al. |
| 9,234,966 B2 | 1/2016 | Sugawara et al. |
| 9,354,333 B2 | 5/2016 | Inoue et al. |
| 9,366,767 B2 | 6/2016 | Inoue et al. |
| 9,423,512 B2 | 8/2016 | Sato et al. |
| 9,445,030 B2 | 9/2016 | Yagi et al. |
| 9,462,989 B2 | 10/2016 | Takenaka et al. |
| 9,468,414 B2 | 10/2016 | Ryu et al. |
| 9,470,800 B2 | 10/2016 | Iwashita et al. |
| 9,470,802 B2 | 10/2016 | Okada et al. |
| 9,541,653 B2 | 1/2017 | Iwashita et al. |
| 9,655,586 B2 | 5/2017 | Yagi et al. |
| 9,737,271 B2 | 8/2017 | Iwashita et al. |
| 9,812,474 B2 | 11/2017 | Yagi et al. |
| 2010/0148080 A1 | 6/2010 | Endo et al. |
| 2011/0155899 A1 | 6/2011 | Dror et al. ................. 250/252.1 |
| 2011/0317054 A1 | 12/2011 | Kameshima et al. |
| 2012/0112087 A1 | 5/2012 | Yokoi ........................ 250/394 |
| 2012/0112088 A1 | 5/2012 | Abraham ................... 250/395 |
| 2013/0187054 A1 | 7/2013 | Ishii et al. |
| 2013/0221198 A1 | 8/2013 | Sawada et al. |
| 2014/0034836 A1 | 2/2014 | Takei et al. |
| 2014/0112448 A1 | 4/2014 | Takenaka et al. |
| 2014/0239186 A1 | 8/2014 | Sato et al. |
| 2014/0361189 A1 | 12/2014 | Kameshima et al. |
| 2016/0084969 A1 | 3/2016 | Sato et al. |
| 2016/0178764 A1 | 6/2016 | Ryu et al. |
| 2016/0270755 A1 | 9/2016 | Takenaka et al. |
| 2016/0305818 A1 | 10/2016 | Ichikawa et al. .......... 250/208.1 |
| 2017/0285189 A1 | 10/2017 | Ryu et al. |
| 2017/0303878 A1 | 10/2017 | Iwashita et al. |

FOREIGN PATENT DOCUMENTS

| | | |
|---|---|---|
| JP | A 2013-516610 | 5/2013 |
| WO | WO 2015/087663 | 6/2015 |

[Fig. 1]
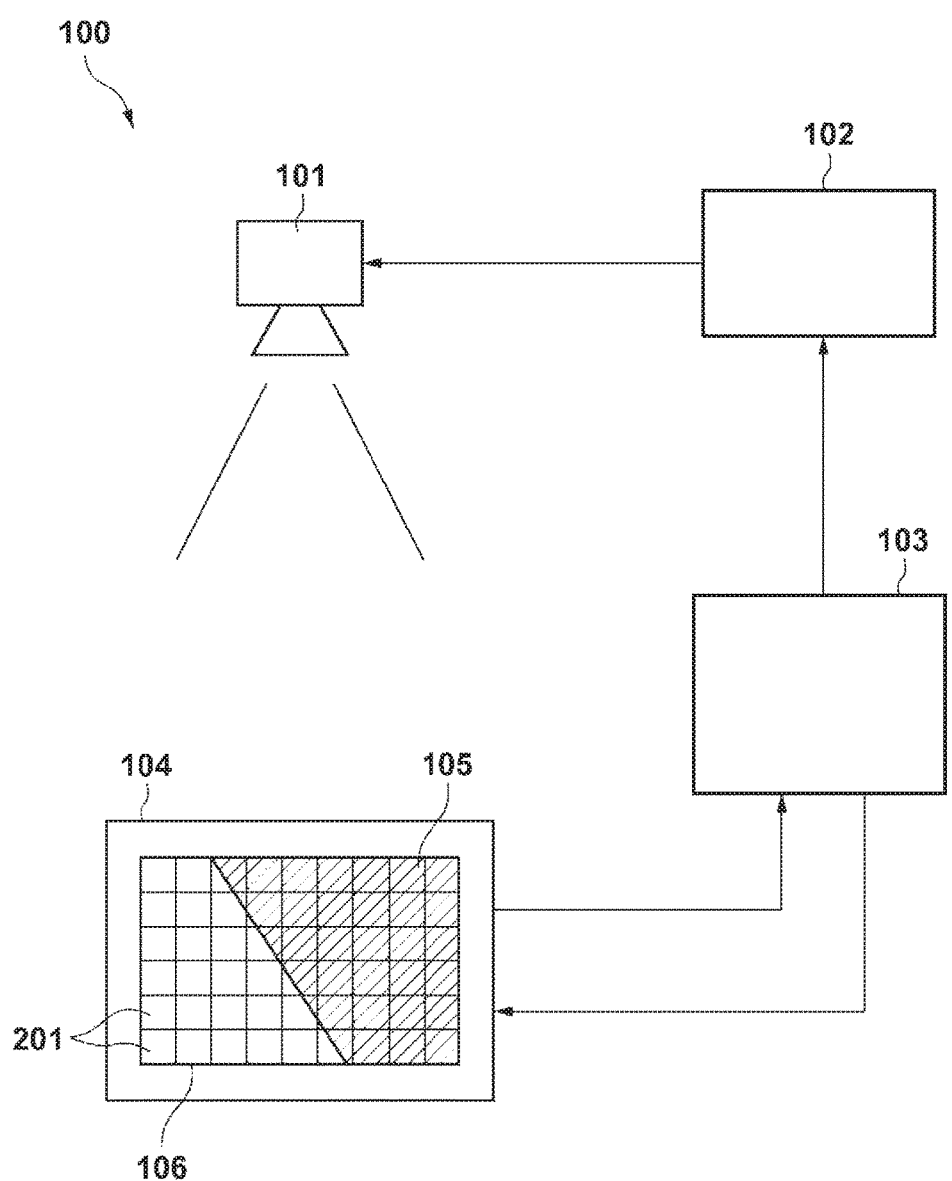

[Fig. 2]
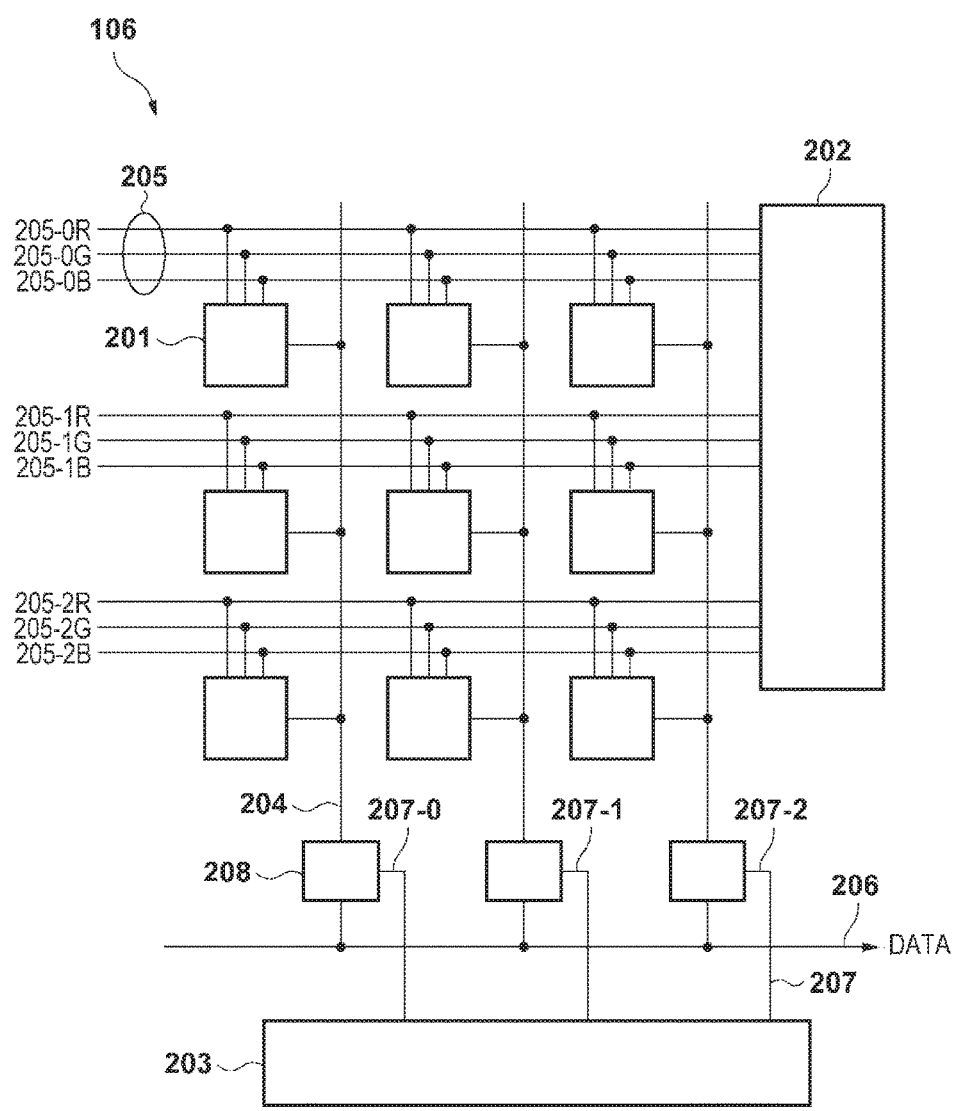

[Fig. 3]
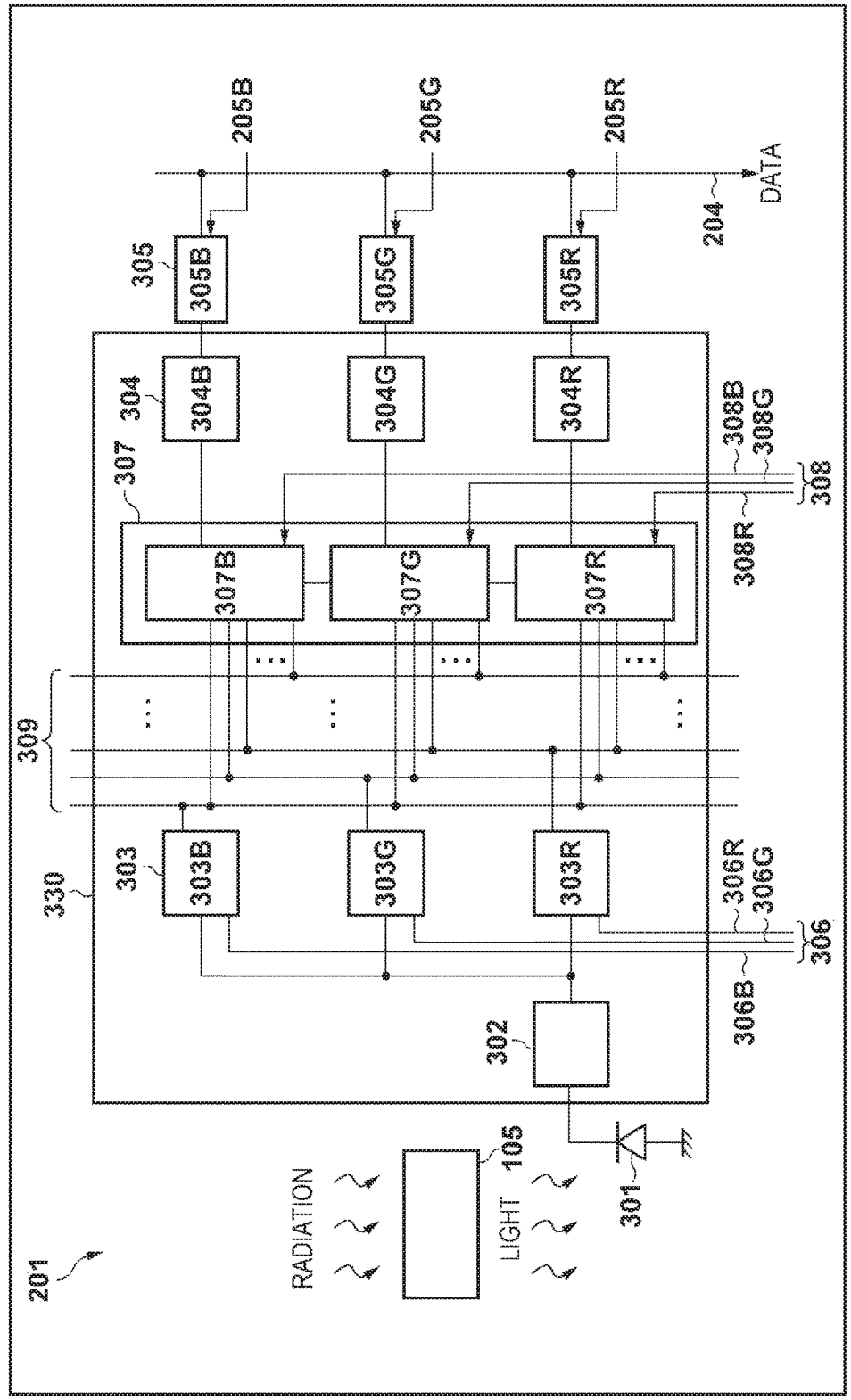

[Fig. 4]
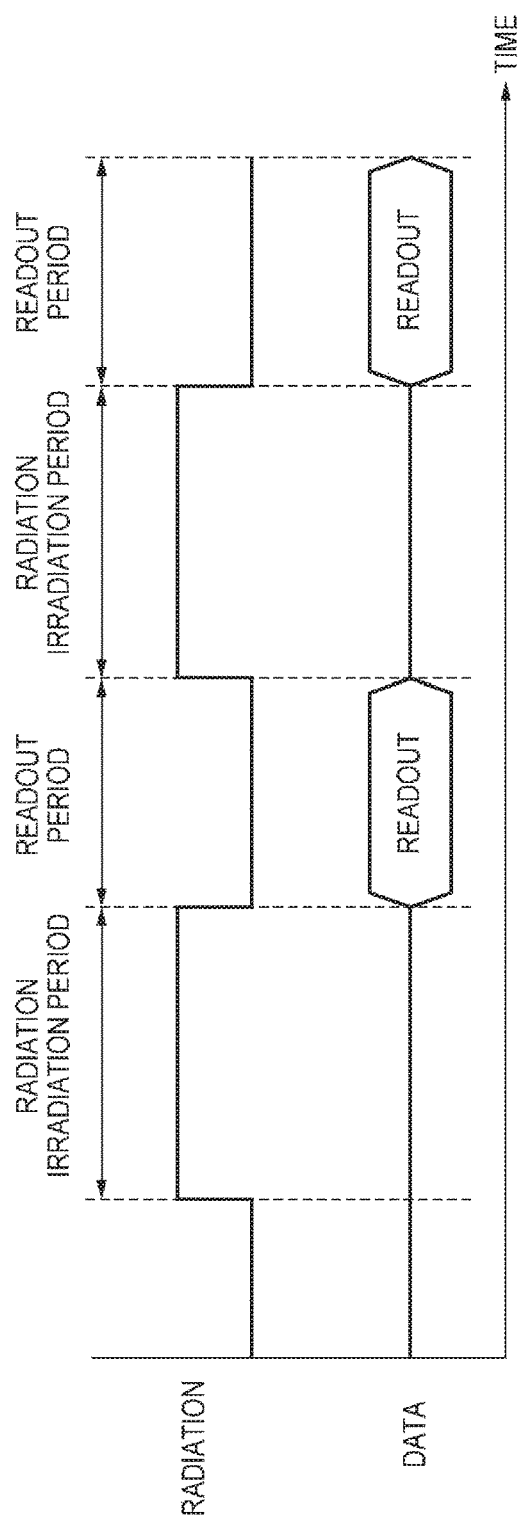

[Fig. 5]
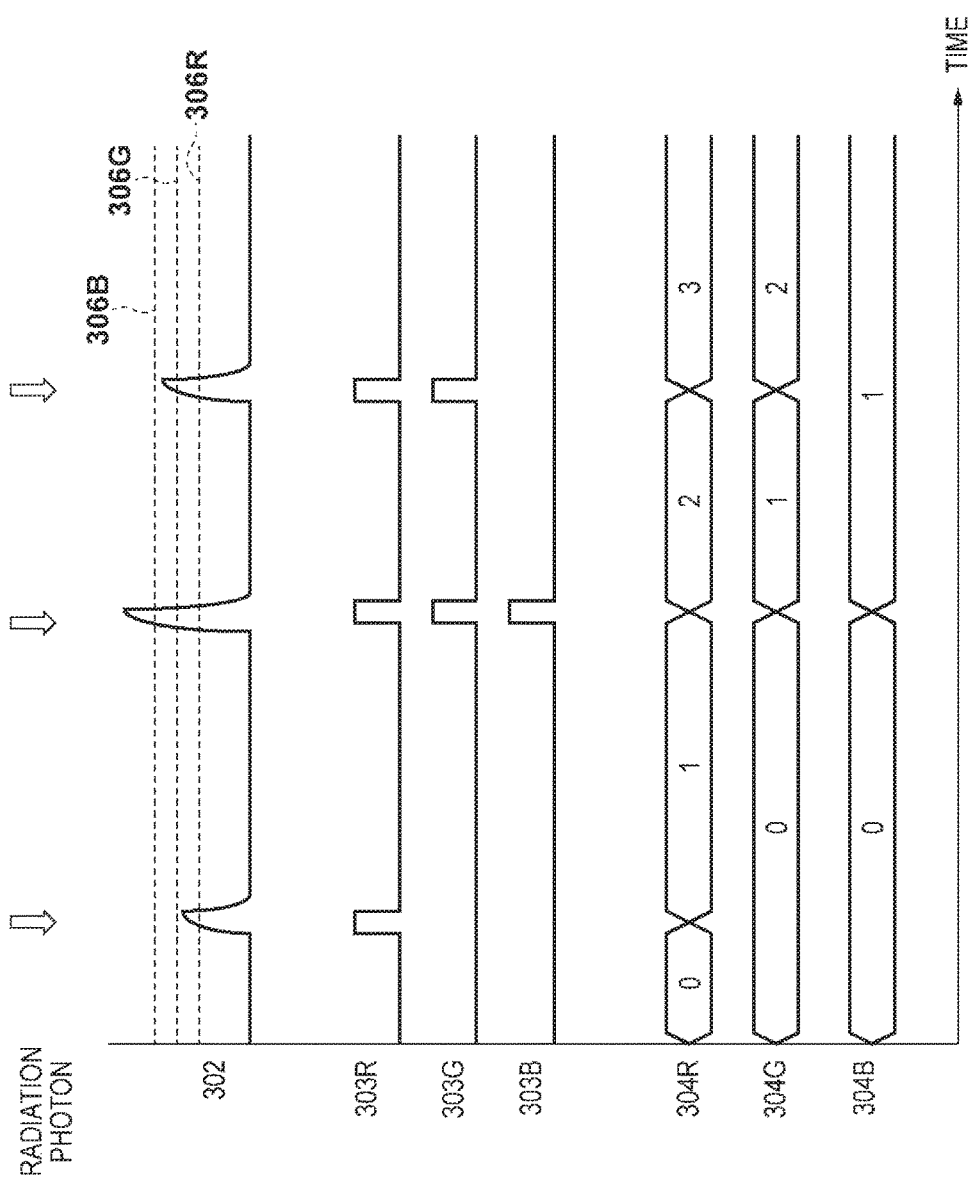

[Fig. 6]
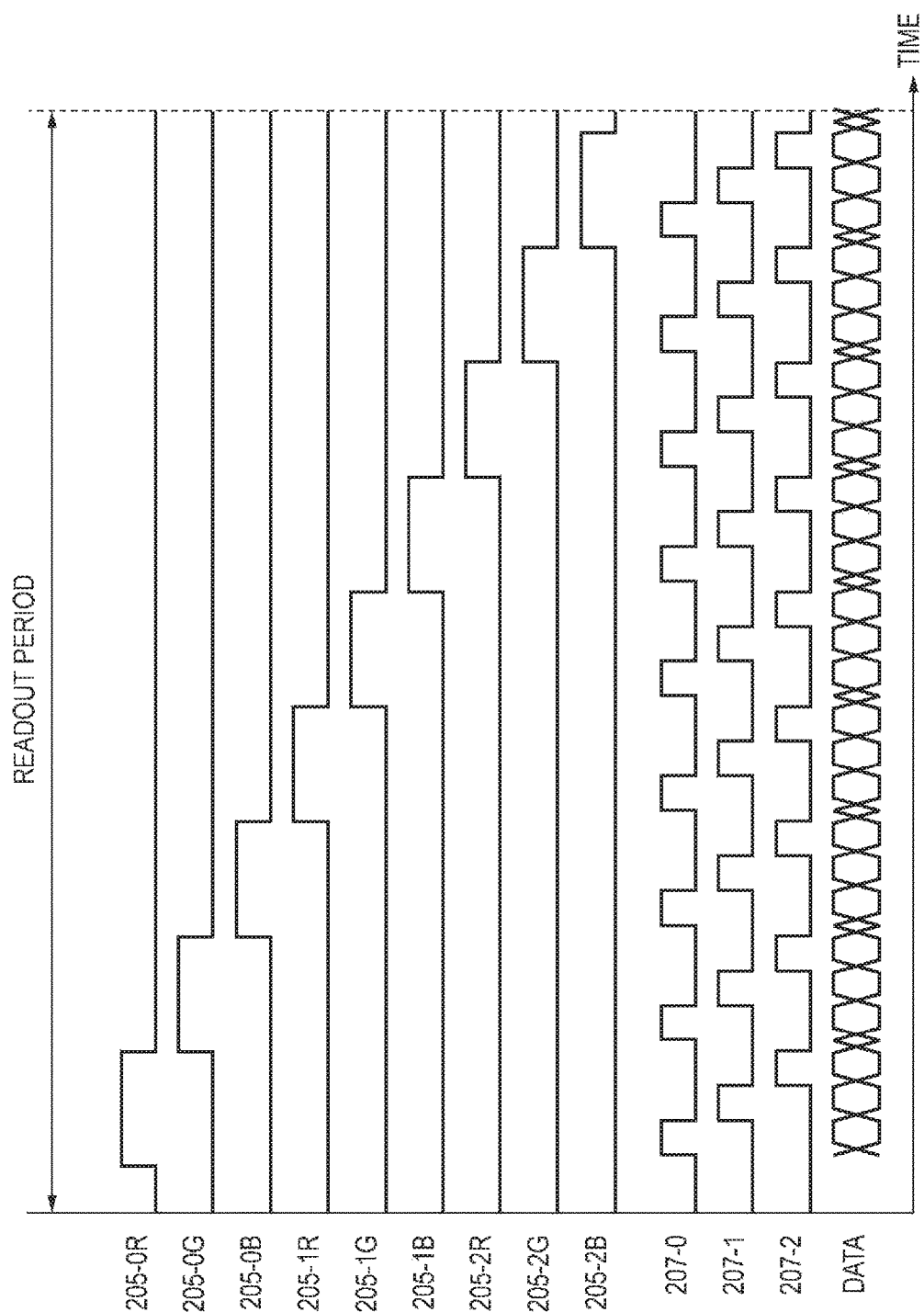

[Fig. 7]
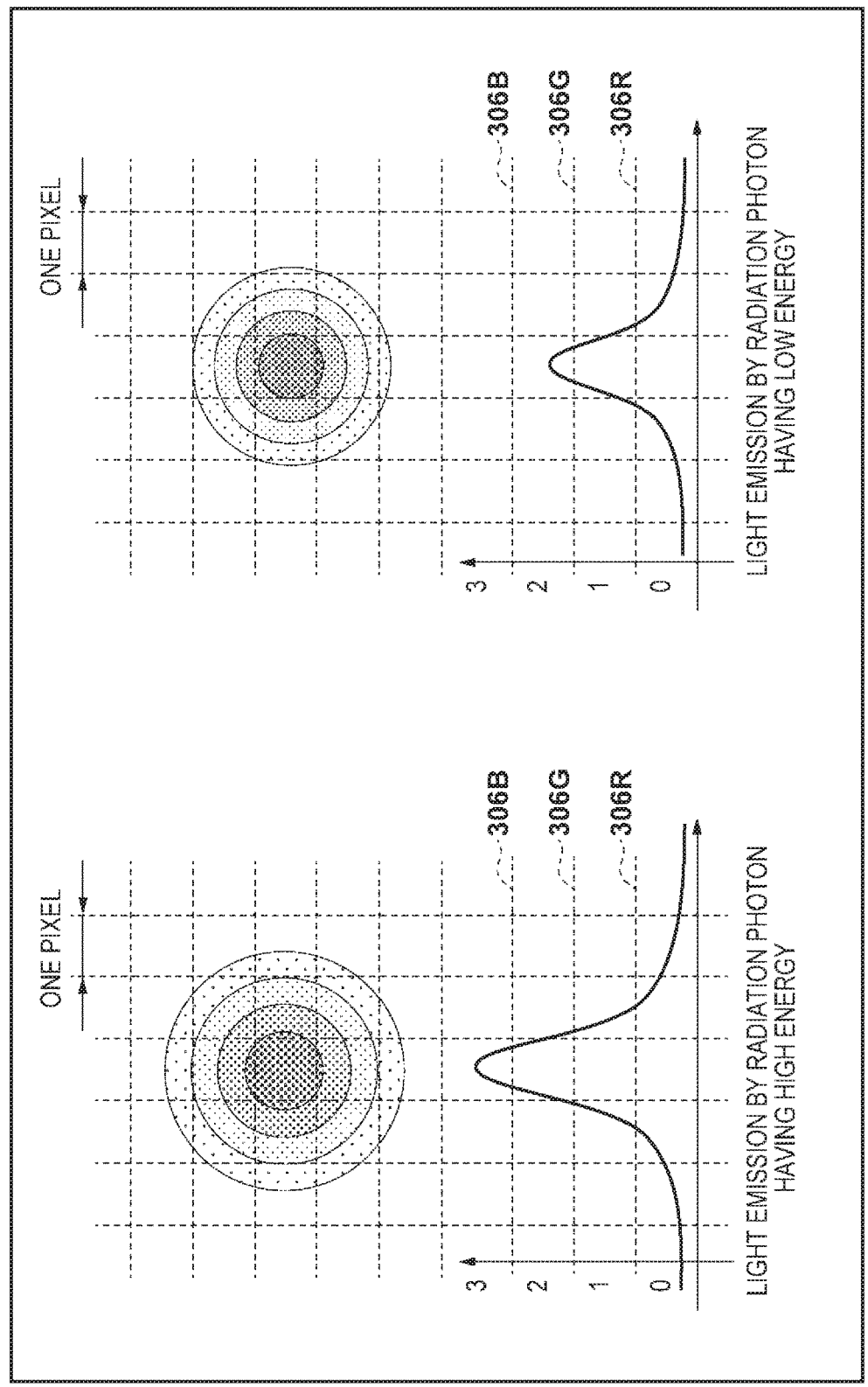

[Fig. 8]
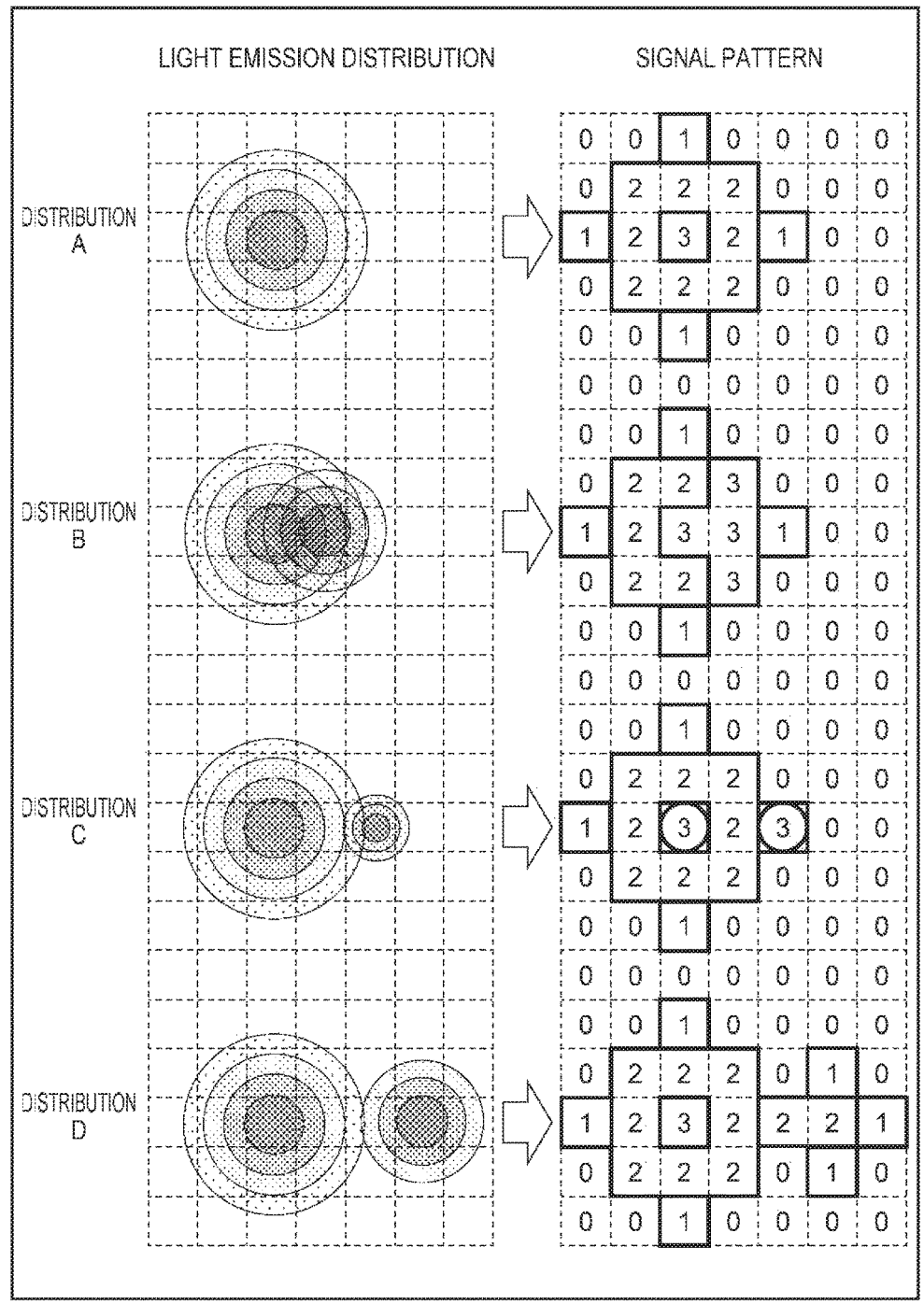

[Fig. 9]
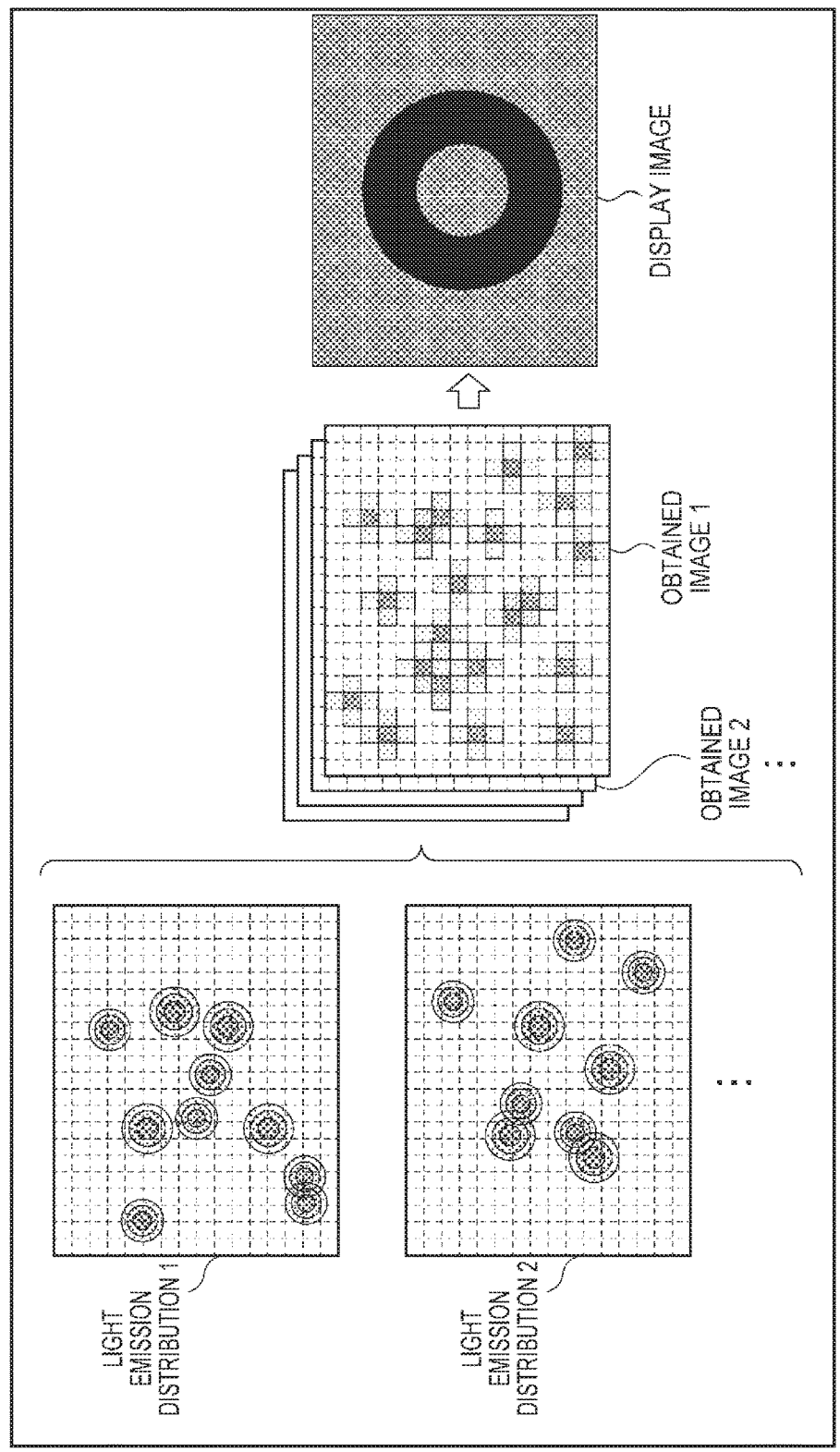

[Fig. 10]
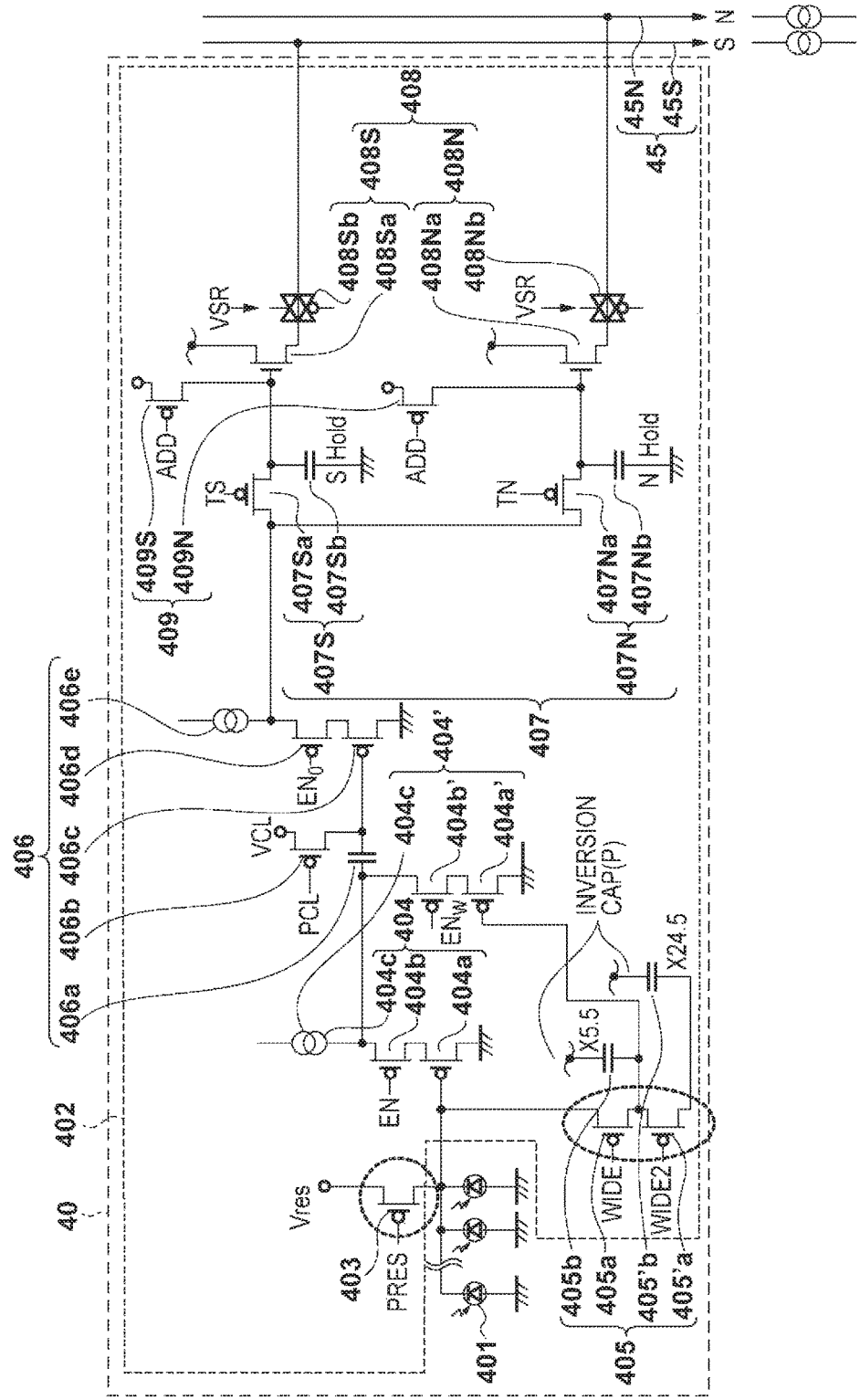

RADIATION IMAGING APPARATUS, CONTROL METHOD THEREOF, AND NON-TRANSITORY COMPUTER-READABLE STORAGE MEDIUM

TECHNICAL FIELD

The present invention relates to a radiation imaging apparatus, a control method thereof, and a program.

BACKGROUND ART

There is known a radiation imaging apparatus that uses, as an imaging apparatus used for medical imaging diagnosis or non-destructive inspection by radiation, a flat panel detector (to be referred to as FPD hereinafter) formed from a semiconductor material. Such a radiation imaging apparatus can be used, for example, in medical imaging diagnosis, as a digital imaging apparatus for obtaining a still image or a moving image.

An integral sensor and a photon counting sensor are available as a radiation detection method used for FPDs. An integral sensor measures the total amount of charges generated from incident radiation. Meanwhile, a photon counting sensor identifies the energy (wavelength) of incident radiation and obtains the detection count of radiation for each energy level. That is, since the photon counting sensor has an energy resolution, the diagnosis capability can be improved compared to the integral sensor.

Japanese Patent Laid-Open No. 2013-516610 proposes a direct type photo counting sensor that directly detects radiation in each pixel by using CdTe. In addition, Japanese Patent Laid-Open No. 2003-279411 proposes an indirect type photo counting sensor that converts incident radiation into light by a scintillator and detects the light converted, from the radiation in each pixel.

SUMMARY OF INVENTION

Single crystal CdTe used in a direct type sensor can only grow to about a few cm square. Therefore, it is difficult and very costly to increase the area of a direct type sensor. Although there is a method of implementing a direct type sensor with a large area by depositing amorphous Se, a sensor manufactured by this method operates slowly and requires temperature management.

Meanwhile, an indirect type sensor is advantageous since it is easy to increase the area and low in cost. However, pileup is likely to occur in the indirect type sensor. Pileup is a phenomenon in which a plurality of radiation photons are detected simultaneously by the same pixel in the sensor and are detected as a single radiation photon. In this case, the sensor erroneously determines the detection count of the radiation and energy of incident radiation.

For the indirect type sensor, light converted from the radiation photons by a scintillator diffuses in the scintillator and is detected in respective pixels. The indirect type sensor may simultaneously detect, in one pixel, light which is converted from different radiation photons incident on nearby pixels simultaneously and spreads in the scintillator, and detect it as light emission converted from a single radiation photon. Owing to the influence of light diffusion, the occurrence frequency of pileup is higher in the indirect type sensor than in the direct type sensor.

Japanese Patent Laid-Open No. 2013-516610 discloses a sensor in which counters having a different energy threshold for each pixel are arranged with respect to an incident radiation photon in a direct type sensor. Japanese Patent Laid-Open No. 2013-5116610 discloses a technique of estimating occurrence of pileup by comparing the counts of the detected different energy thresholds in the respective pixels. However, Japanese Patent Laid-Open No. 2013-516610 does not describe the fact that a plurality of radiation photons incident on the nearby pixels are detected in the same pixel in the sensor owing to the influence of light diffusion and are detected as a single radiation photon. Japanese Patent Laid-Open No. 2003-279411 which discloses an indirect type sensor does not describe pileup.

Some embodiments of the present invention provide a technique advantageous in detecting pileup in an indirect type photon counting sensor.

According to some embodiments, a radiation imaging apparatus comprising: a scintillator configured to convert radiation into light; a sensor panel in which a plurality of pixels each comprising a light detector configured to detect the light is arranged in a two-dimensional array; and a processing unit, wherein the processing unit comprises a signal generating unit configured to output signals indicating intensities of the light detected by the light detector of each of the plurality of pixels, and a detection unit configured to identify a group of pixels each of which outputs a signal of a level exceeding a reference value out of the signals and detect, based on a pattern of the group, pileup in which a plurality of radiation photons is detected as a single radiation photon, is provided.

According to some other embodiments, a control method of a radiation imaging apparatus that comprises a scintillator configured to convert radiation into light and a sensor panel in which a plurality of pixels each comprising a light detector configured to detect the light is arranged in a two-dimensional array, the method comprising: outputting signals indicating intensities of the light detected by the light detectors of the plurality of pixels; identifying a group of pixels each of which outputs a signal of a level exceeding a reference value out of the signals; and detecting, based on a pattern of the group, pileup in which a plurality of radiation photons is detected as a single radiation photon, is provided.

Further features of the present invention will become apparent from the following description of exemplary embodiments (with reference to the attached drawings).

BRIEF DESCRIPTION OF DRAWINGS

FIG. 1 is a block diagram showing an example of the arrangement of a radiation imaging apparatus according to the present invention;

FIG. 2 is a block diagram showing the arrangement of a sensor panel of the radiation imaging apparatus in FIG. 1;

FIG. 3 is a block diagram showing the arrangement of a pixel of the radiation imaging apparatus in FIG. 1;

FIG. 4 is a timing chart showing an irradiation period a readout period of the sensor panel of the radiation imaging apparatus in FIG. 1;

FIG. 5 is a timing chart showing an operation of each pixel in the irradiation period of the radiation imaging apparatus in FIG. 1;

FIG. 6 is a timing chart showing an operation of each pixel n the readout period of the radiation imaging apparatus in FIG. 1;

FIG. 7 shows views of a light emission distribution of a scintillator of the radiation imaging apparatus in FIG. 1;

FIG. 8 is a view showing light emission distributions converted to signals of a plurality of levels of the radiation imaging apparatus in FIG. 1;

FIG. 9 shows views of an example of obtained images of the radiation imaging apparatus in FIG. 1; and FIG. 10 is a view showing the arrangement of a pixel in a radiation imaging apparatus according to the present invention.

DESCRIPTION OF EMBODIMENTS

Detailed embodiments of a radiation imaging apparatus according to the present invention will be described below with reference to the accompanying drawings. Note that in the following description and drawings, common reference numerals denote common components throughout a plurality of drawings. Hence, the common components will be described by cross-referring to the plurality of drawings, and a description of components denoted by common reference numerals will appropriately be omitted. Note that radiation according to the present invention can include not only α-rays, β-rays, and γ-rays that are beams generated by particles (including photons) emitted by radioactive decay but also beams having energy equal to or higher than the energy of these beams, for example, X-rays, particle beams, and cosmic rays.

A radiation imaging apparatus 100 (also referred to as a "radiation imaging system") according to a first embodiment of the present invention will be described. FIG. 1 shows an example of the arrangement of the radiation imaging apparatus 100 according to this embodiment. The radiation imaging apparatus 100 includes, for example, an irradiating unit 101 that irradiates an object with radiation, an irradiation control unit 102 that controls the irradiating unit 101, an imaging unit 104 for imaging the object irradiated with radiation, and a processor 103. Each of the irradiation control unit 102 and the processor 103 can be formed by, for example, a computer which includes a CPU, a memory, and the like. Although the irradiation control unit 102 and the processor 103 are formed separately in this embodiment, the present invention is not limited to this, and they may be formed integrally. That is, the irradiation control unit 102 and the processor 103 can be formed by one computer including these functions.

The imaging unit 104 includes, for example, a scintillator 105 that converts incident radiation into light and a sensor panel 106. In the sensor panel 106, for example, a plurality of pixels 201 each detecting light converted from radiation by the scintillator 105 are arranged in a two-dimensional array so as to form a plurality of rows and a plurality of columns. Each pixel 201 (to be described in detail later) has an arrangement for performing photon counting radiation imaging and counts the number of photons of incident radiation based on each light detection result.

The processor 103 exchanges a signal or data with the imaging unit 104. More specifically, the processor 103 controls the imaging unit 104 to perform radiation imaging and receives a signal obtained by the operation from the imaging unit 104. The signal includes counted values of radiation photons. For example, the processor 103 generates, based on the counted values, image data for displaying a captured image by radiation on a display unit (not shown) such as a display or the like. In this case, the processor 103 can perform predetermined correction processing on the image data. In addition, the processor 103 supplies, to the irradiation control unit 102, a signal to start or end radiation irradiation.

Next, the arrangement of the sensor panel 106 will be described with reference to FIG. 2. FIG. 2 is a block diagram showing the arrangement of the sensor panel 106. The sensor panel 106 may include, for example, the plurality of pixels 201, a vertical scanning circuit 202, a horizontal scanning circuit 203, column signal lines 204, signal lines 205, an output line 206, signal lines 207, and column selection circuits 208. Each of the plurality of pixels 201 may be configured to obtain the detection count of light generated in the scintillator 105 for each of a plurality of levels related to the intensity of light. When a signal is supplied to each pixel 201 via the corresponding signal line 205, selected detection count data for each level according to the intensity of the detected light is output from each pixel 201 to the corresponding column selection circuit 208 via the corresponding column signal line 204.

The vertical scanning circuit 202 sequentially switches the signal lines 205 which supply signals so that the detection count data of a desired level out of a plurality of levels will be output from each pixel 201. If a signal is supplied to each column selection circuit 208 via the corresponding signal line 207, the detection count data output from each corresponding pixel 201 is output as data DATA to the output line 206. In addition, the horizontal scanning circuit 203 sequentially switches the signal lines 207 which supply signals so that the operation to output the detection count data to the output line 206 will be sequentially performed by the plurality of column selection circuits 208. Although the sensor panel 106 arranged with 3 rows×3 columns of pixels 201 has been shown for the sake of descriptive convenience in FIG. 2, a sensor panel 106 arranged with a larger number of pixels 201 can be used as well. For example, in a 17 inch sensor panel 106 (FPD), approximately 2,800 rows×2,800 columns of pixels 201 can be arranged in a two-dimensional array.

The arrangement of each pixel 201 will be described next with reference to FIG. 3. FIG. 3 is a block diagram showing the arrangement of each pixel 201. Each pixel 201 of the sensor panel 106 can include, for example, a light detector 301, a processing unit 330, output units 305, and a reference voltage unit that supplies reference voltages 306. The processing unit 330 can also include a voltage conversion unit 302, comparison units 303, memories 304, and detection units 307. The light detector 301 is a photoelectric converter that generates a signal by detecting light generated in the scintillator 105 when the radiation enters the scintillator 105. A known photoelectric conversion element such as a photodiode or the like can be used as the light detector 301. For example, a differential circuit is used as the conversion unit 302. The voltage conversion unit 302 is, for example, a differential circuit, and converts a signal generated by the light detector 301 into a pulse signal as a voltage signal and outputs the converted pulse signal to each comparison unit 303. Each comparison unit 303 compares the voltage of the pulse signal output from the voltage conversion unit 302 with the corresponding reference voltage 306 and generates, for example, a binary signal as a comparison result signal in accordance with the comparison result. If the voltage of the pulse signal output from the voltage conversion unit 302 is equal to or more than the voltage of each reference voltage 306, the corresponding comparison unit 303 outputs a digital value "1" as the signal in accordance with the comparison result. Meanwhile, if the voltage of the pulse signal output from the voltage conversion unit 302 is less than each reference voltage 306, the corresponding comparison unit 303 outputs a digital value "0" as the signal in accordance with the comparison result. Each reference voltage 306 which is supplied to the corresponding comparison unit 303 may be set to be a common value for all of the pixels 201 in the sensor panel 106. If radiation enters the scintillator 105 and is converted into light, each comparison unit 303 generates a binary digital value signal, via the voltage conversion unit 302, in accordance with the light detected by the light detector 301. The voltage conversion unit 302 and the comparison units 303 thus form a signal generating unit.

In the arrangement shown in FIG. 3, three comparison units 303B, 303G, and 303R are arranged in each pixel 201, and reference voltages 306B, 306G, and 306R having different values are supplied to the respective comparison units 303B, 303G, and 303R. Each pixel 201 can output the signals of the plurality of levels in accordance with the intensity of light by the plurality of comparison units 303 and reference voltages 306. In the arrangement of FIG. 3, for example, each pixel 201 may output, by including three comparison units 303 and reference voltages 306, signals of four levels in accordance with the intensity of incident light including a case in which no light is detected.

The detection units 307 obtain a signal pattern 309 that includes the signals of the plurality of levels output from the comparison units 303 of the plurality of pixels 201 in the same period. More specifically, each detection unit 307 extracts the pixel that outputs a detection signal as a signal which exceeds a reference value indicating that light is detected, out of the signals of the plurality of levels output from the plurality of pixels 201. Then, each detection unit 307 identifies a group formed by one pixel of interest and one or more pixels continuous from the pixel of interest that outputs the detection signal indicating that light is detected in the same period. Then, each detection unit 307 determines whether the signal pattern 309 of the obtained group is a signal pattern obtained by the signal radiation photon or a signal pattern where pileup occurs in which the plurality of radiation photons enter in the same period and are detected as the single radiation photon. This determination is performed by comparing whether the identified group satisfies one or more determination criteria 308 indicating preset pileup. Each detection unit 307 detects pileup based on this determination result.

Each determination criterion 308 indicating pileup is related to, for example, the number of pixels 201 that form the group, the arrangement of the pixels 201 that form the group, and the intensity of incident light of the detection signal output from each pixel 201 of the group. The plurality of determination criteria 308 may be provided. Each detection unit 307 detects pileup by determining whether at least any condition for the signal pattern 309 of the group as described above satisfies one or more determination criteria 308 indicating pileup. The determination criteria 308 may also be changed arbitrarily in accordance with, for example, the characteristics of the sensor panel 106 in the radiation imaging apparatus 100 or imaging conditions. The determination criteria 308 for detecting pileup will be described later.

The memories 304 are arranged at the subsequent stages of the respective detection units 307. In order to generate the captured image, the processing unit 330 of each pixel 201 obtains the output count of the detection signal for each of the plurality of levels indicating the intensity of light. If pileup is not detected in the group, in accordance with each level of the detection signal, the processing unit 330 counts the number of times each pixel 201 that forms the group outputs the detection signal and stores the count in each memory 304. If pileup is detected in the group, the processing unit 330 may not count the number of times each pixel 201 that forms the group outputs the detection signal so as not to erroneously determine the detection count of radiation and energy of incident radiation. If the detection signal is output in one pixel of interest and the detection signal is not output in the pixel adjacent to the pixel of interest, the processing unit 330 may count, assuming that no pileup is detected, the number of times the detection signal is output from the pixel of interest in accordance with each level of the detection signal.

In the arrangement shown in FIG. 3, three detection units 307B, 307G, and 307R are arranged in each pixel 201 and provided with determination criteria 308B, 308G, and 308R each indicating different pileup. Memories 304B, 304G, and 304R are connected to the respective detection units 307B, 307G, and 307R. Note that if the respective detection units 307 arranged in each pixel 201 are connected to each other and, for example, satisfy at least one determination criterion out of the plurality of determination criteria, the detection units 307 may determine that pileup is detected.

When the signal is supplied from the vertical scanning circuit 202 via each signal line 205, the corresponding output unit 305 obtains the output count of the detection signal in accordance with whether pileup is detected and supplies data DATA stored in each memory 304 to the corresponding column selection circuit 208 via the corresponding column signal line 204. Then, data DATA is output to the processor 103 when the signal is supplied to each column selection circuit 208 via the corresponding signal line 207.

In the arrangement shown in FIG. 3, three comparison units 303 are arranged in each pixel 201. However, the arbitrary number of comparison units 303 may be arranged and given different reference voltages. For example, when one comparison unit 303 is arranged, the comparison unit 303 can output, to the corresponding detection unit 307, signals of two levels, namely, a case in which light is detected and a case in which light is not detected. Three detection units 307 are arranged in each pixel 201. However, the arbitrary number of detection units 307 may be arranged and detect pileup by using the different determination criteria 308. Similarly, the arbitrary number of memories 304 may be arranged. For example, the output count of the detection signals according to the intensities of light of the plurality of levels may be obtained in accordance with the presence/absence of pileup and stored in one memory 304.

Driving of the radiation imaging system according to this embodiment will be described next. FIG. 4 is a timing chart showing the timing of driving the sensor panel 106 of the imaging unit 104. The waveforms in FIG. 4 represent the radiation irradiation period and the readout period of data DATA with respect to the abscissa representing the time. In FIG. 4, the radiation irradiation period is a period in which the irradiating unit 101 irradiates the object with radiation. In this period, the radiation that has entered the sensor panel 106 is converted into light by the scintillator 105, and the number of times the detection signals are output for the respective signals of the plurality of levels according to the intensities of light is counted in accordance with whether pileup is detected. The readout period is a period in which data DATA, which is the count obtained during the radiation irradiation period, is output from the sensor panel 106. As shown in FIG. 4, the sensor panel 106 can obtain a moving image by alternately performing the radiation irradiation period and the readout period. In addition, for example, a still image can be obtained by performing the radiation irradiation period and the readout period once.

The operation during the irradiation period in the pixel 201 arranged as shown in FIG. 3 will be described next with reference to FIG. 5. FIG. 5 is a timing chart showing the operation of each pixel 201 during the radiation irradiation period. The waveforms in FIG. 5 represent the output of the voltage conversion unit 302, the outputs of the comparison units 303, and the output count of the detection signals stored in the memories 304 with respect to the abscissa representing the time. If the voltage of the pulse signal output from the voltage conversion unit 302 is equal to or more than the reference voltage 306R, the digital value "1" is output, as the detection signal, from the comparison unit 303R. Then, if pileup is not detected in the corresponding detection unit 307, the memory 304R obtains the output count of the digital value "1" from the comparison unit 303R. Meanwhile, if the voltage of the pulse signal output from the voltage conversion unit 302 is equal to or more than the reference voltage 306G, the digital value "1" is output, as the detection signal, from each of the comparison units 303G and 303R. Then, if pileup is not detected in the corresponding detection unit 307, each of the memories 304G and 304R obtains the output count of the digital value "1" from each of the comparison units 303G and 303R. Similarly, if the voltage of the pulse signal output from the voltage conversion unit 302 is equal to or more than the reference voltage 306B, the digital value "1" is output, as the detection signal, from each of the comparison units 303B, 303G, and 303R. Then, if pileup is not detected in the corresponding detection unit 307, each of the memories 304B, 304G, and 304R obtains the output count of the digital value "1" from each of the comparison units 303B, 303G, and 303R. As described above, the output count of the detection signal from the voltage conversion unit 302 is obtained in accordance with whether pileup is detected for each of the plurality of reference voltages 306. This allows each pixel 201 to obtain the detection count of light generated in the scintillator 105 by incident radiation for each of the plurality of levels according to the intensities of light.

The operation during the readout period of each pixel 201 arranged as shown in FIG. 3 will be described next with reference to FIG. 6. FIG. 6 is a timing chart showing the operation of each pixel 201 during the readout period. The waveforms in FIG. 6 represent the signal supply to each signal line 205, the signal supply to each signal line 207, and the output of data. DATA obtained from each column selection circuit 208 with respect to the abscissa representing the time. As shown in FIG. 6, signals are sequentially supplied to the plurality of signal lines 205 and the plurality of signal lines 207. For example, when a signal supply operation to a signal line 205-0R is started, data indicating the output count of the detection signal in accordance with whether pileup is detected is supplied from an output unit 305R of each pixel 201 connected to the signal line 205-0R to a corresponding one of the column selection circuits 208. Then, during the signal supply period of the signal line 205-0R, signals are sequentially supplied to the plurality of signal lines 207, and data DATA are sequentially output from the plurality of column selection circuits 208 to the output line 206.

The determination criteria 308 for detecting pileup will be described next with reference to FIGS. 7 to 9. FIG. 7 shows a light emission distribution when one radiation photon is converted into light by the scintillator 105. The scintillator 105 converts incident radiation photon into light. The converted light diffuses in the scintillator. Accordingly, each light detector 301 of the plurality of pixels 201 may detect light generated by the single radiation photon. The intensity of light converted from a radiation photon may depend on the energy of the radiation photon. A radiation photon having a short wavelength has high energy, and thus its light emission is high in intensity and large in amount. As shown in FIG. 7, the distribution or the intensity of the light detected by the light detector 301 of each pixel 201 may be different between light converted from a high-energy radiation photon and light converted from a low-energy radiation photon.

The comparison units 303R, 303G, and 303B arranged in each pixel 201 convert the light detected by the light detector 301 into the signals of the plurality of levels according to the intensities of light. In this embodiment, level 0 indicates that the digital value "0" is output, as the signal in accordance with the above-described comparison result, from each of all the comparison units 303R, 303G, and 303B. Level 1 indicates that the digital value "1" is output from the comparison unit 303R, and the digital value "0" is output from each of the comparison units 303G and 303B. Similarly, level 2 indicates that the digital value "1" is output from each of the comparison units 303R and 303G, and the digital value "0" is output from the comparison unit 303B, and level 3 indicates that the digital value "1" is output from each of all the comparison units 303R, 303G, and 303B. That is, level 0 indicates that the voltage of the pulse signal output from the voltage conversion unit 302 by the light detected in each pixel 201 is lower than the reference voltage 306R. Level 1 indicates that the voltage of the pulse signal output from the voltage conversion unit 302 is between the reference voltages 306R and 306G. Similarly, level 2 indicates that the voltage of the pulse signal output from the voltage conversion unit 302 is between the reference voltages 306G and 306B, and level 3 indicates that the voltage of the pulse signal output from the voltage conversion unit 302 is equal to or more than the reference voltage 306B. The detected light is thus converted into the signals of the plurality of levels.

FIG. 8 shows an example of light emission distributions converted from the radiation photons and signal patterns converted into signals of the plurality of levels according to the intensities of light by the processing unit 330. FIG. 8 shows the light emission distributions converted from the radiation photons on the left side and the converted signal patterns on the right side. The sensor panel 106 is obtained by arranging the plurality of pixels 201 in the two-dimensional array, and outputs, from the respective pixels 201, the signals of the plurality of levels according to the distributions and the intensities of light emission in the scintillator 105. In this embodiment, level 0 represents a signal with no light emission being detected, and each of levels 1 to 3 represents a detection signal with light emission being detected. Levels 3, 2, and 1 represent the intensity of light in descending order. Level 3 indicates the highest intensity of light. As described above, the light converted from the radiation photons diffuses in the scintillator 105, and thus is detected in the plurality of pixels 201. The signal pattern 309 obtained from the group that outputs the detection signal indicating that light is detected in this case becomes, for example, the signal patterns as shown in FIG. 8. A distribution A of FIG. 8 is an example of the signal pattern of the group obtained from the light emission distribution converted from the single radiation photon. A signal indicating the high intensity of light is output from the pixel 201 near the center of the group and a signal indicating the low intensity of light is output from the peripheral pixel 201. Meanwhile, each of distributions B to D of FIG. 8 is an example of the signal pattern of the group where pileup occurs in which the plurality of radiation photons are detected simultaneously by the same pixel in the sensor and are detected as the single radiation photon. If the signal pattern converted from the plurality of radiation photons is detected as a conversion pattern converted from the single radiation photon, the output count of the detection signal for each of the plurality of levels according to the intensities of light and energy of incident radiation may be determined erroneously. For example, the incident count of one radiation photon is obtained even though two or more radiation photons have entered. For example, because light emission is caused by the plurality of radiation photons, it may be determined that the high-energy radiation photon enters. This may cause poor image quality of the captured image. For example, it may become impossible to accurately perform correction processing such as a process of increasing a resolution by removing diffusion of light by the scintillator 105 when the signal pattern 309 is converted into a digital distribution.

In order to suppress degradation in the captured image, this embodiment compares whether the signal pattern 309 of the group satisfies one or more determination criteria 308 indicating pileup in each detection unit 307, and pileup is detected based on this determination result. Each determination criterion 308 is set to be a signal pattern unobtainable by converting the signal pattern 309 of the group from the single radiation photon.

For example, the diffusion range of the light converted from the single radiation photon may have an upper limit. Letting the determination criterion 308 be the number of pixels 201 that form the group and output the detection signals, if the number of pixels 201 that output the detection signals is larger than a predetermined number, it may be determined that the determination criterion 308 for detecting pileup is satisfied. The number of pixels 201 the determination criterion 308 is satisfied can be set appropriately in accordance with, for example, the size of each pixel 201 or a spacing at which the pixels 201 are arranged, or the spread amount of the light converted from the radiation photons.

The intensity of the light converted from the single radiation photon may also include an upper limit. If a detection signal of a level higher than a predetermined level at which the intensity of light is converted from the single radiation photon is output to the detection signal output from the group, it may be determined that the determination criterion 308 for detecting pileup is satisfied. For example, for the processing unit 330 that outputs the above-described four levels, it may be determined that pileup is detected if the value of each reference voltage 306 for outputting level 3 is set large, and the detection signal of level 3 having a voltage equal to or more than this reference voltage 306 and the highest intensity of light is output.

A range in which the light converted from the single radiation photon indicates the high intensity of light may also have an upper limit. For example, like the distribution B of FIG. 8, the number of pixels 201 each outputting the detection signal indicating the highest-level intensity of light of the detection signals output from the group may be set as the determination criterion 308. If the number of pixels 201 each outputting the detection signal indicating the highest-level intensity of light is larger than a predetermined number, it may be determined that the determination criterion 308 for detecting pileup is satisfied. The number of pixels 201 the determination criterion 308 is satisfied can be set appropriately in accordance with, for example, the size of each pixel 201 or the spacing at which the pixels 201 are arranged, or the spread amount of the light converted from the radiation photons.

As shown in the distribution A of FIG. 8, the distribution of the light converted from the single radiation photon may have the highest intensity of light in a place where the radiation photons enter and are converted into light, and be formed into a circular shape or an elliptical shape and have the low intensity of light in surroundings. Therefore, a possibility is low that the plurality of detection signals each indicating the high-level intensity of light of the detection signal output from the group are interspersed, as shown in the distribution C of FIG. 8. If the level of each detection signal output from the group has two or more peaks, it may be determined that pileup is detected. Since the light emission distribution converted from the single radiation photon may be the circular shape or the elliptical shape, the number of pixels for each row or column that form the group can decrease after the increase in the column or row direction. Therefore, it may be determined that pileup is detected if the number of pixels for each row or column increases after the decrease in the column or row direction in the arrangement of the pixels that form the group, as shown in the distribution D of FIG. 8.

The determination criterion 308 indicating pileup can be set in accordance with, for example, the number of pixels 201 that form the signal pattern 309 of the group, the arrangement of the pixels 201, or the level indicating the intensity of incident light of the detection signal output from each pixel 201. The detection units 307 may perform determinations by using the plurality of determination criteria 308. For example, if the group satisfies at least one determination criterion 308 out of the plurality of determination criteria 308, the detection units 307 may determine that pileup is detected. By using the plurality of determination criteria 308, detection omission of pileup and thus the poor image quality of the obtained captured image is suppressed.

FIG. 9 shows an example of obtained images of the radiation imaging apparatus 100. The output count of the detection signal for each of the plurality of levels according to the intensities of light during the radiation irradiation period is obtained in accordance with whether pileup is detected. The counts for the respective intensities of light in the respective pixels 201 of the obtained images obtained for every single period (frame) are superimposed on each other with respect to the light emission distribution in the scintillator 105. For example, color separation according to energy of incident radiation is performed by superimposing the counts obtained for the respective intensities of light on each other to obtain an image, such as a color image, according to energy. Data DATA of the detection count output from each pixel 201 is transferred from the imaging unit 104 to the processor 103, displaying a final image. In this embodiment, the counts are stored in the memories 304 arranged in each pixel 201 and a sum value is output. A method of obtaining the output count of the detection signals is not limited to this method. For example, for every single period (frame) decided by the operating frequency of each pixel 201 during the radiation irradiation period, signals from the detection units may be output to the processor 103 and the output count of the detection signals in the processor 103 may be obtained.

Imaging may be performed such that the number of radiation photons incident on each pixel 201 becomes one or less in one period by the operation speed of the pixel 201. Pileup can be suppressed by decreasing a dose per one period and performing imaging with the high operating frequency of each pixel 201. For example, the operating frequency of each pixel 201 can be set in the range of 10 kHz to a few (for example, about 100 kHz). Alternatively, the irradiation amount of the irradiating unit 101 can be set to a value obtained when the tube voltage is about 100 kV and the tube current is about 10 mA. For example, when the operating frequency of each pixel 201 is 100 kHz, pileup occurs in which the plurality of radiation photons are detected as the single radiation photon if light generated by the plurality of radiation photons enters the same pixel 201 in a period of 0.01 msec.

On the above-described imaging conditions, if each pixel 201 obtains data DATA sufficient for image quality of the captured image, an influence on the captured image is small even if data DATA of a specific pixel in one period (frame) is excluded. Therefore, the number of times each pixel 201 that forms the group detecting pileup as described above detects the detection signal may not be counted. Without counting, it is possible to improve accuracy in identifying energy of incident radiation photons. However, a process performed if pileup is detected is not limited to this. For example, if pileup is detected from the group, a group, where pileup is detected, caused by the plurality of radiation photons is converted into a plurality of groups caused by the respective radiation photons. Then, the number of times the respective pixels 201 that form the plurality of converted groups output the detection signals may be counted. When the group caused by the plurality of radiation photons is separated into the group caused by the single radiation photon, the number of conversion processes increases. However, this can be an advantage in terms of decreasing an exposure dose because the dose of radiation irradiating the object is not wasted.

In order to reduce a time and load needed for the process, the pixel or the group to be a pileup detection target may be narrowed down in advance. For example, the group becomes the pileup detection target only when the number of pixels 201 that form the group and output the detection signals is larger than a predetermined number, and a determination for detecting pileup may not be performed when the number is smaller than the predetermined number. For example, when the detection signal is output in one pixel of interest described above and the detection signal is not output in the pixel adjacent to the pixel of interest, the determination for detecting pileup may not be performed and the output count of the detection signal in the pixel of interest may be obtained. The maximum number of pixels where the determination is not performed can be decided appropriately in accordance with the size of each pixel 201 or the spacing at which the pixels 201 are arranged, or the spread of light.

In this embodiment, the processor 103 obtains the captured image from the sensor panel 106, as shown in FIG. 11. This captured image is obtained by reading out the value of each memory 304 arranged in each pixel 201 of the sensor panel 106 via the output line 206. The obtained captured image may be displayed without any change. However, the present invention is not limited to this, and arbitrary image processing may be performed. For example, image processing in which only the components of direct rays are used for image formation may be performed to remove scattered rays without using a grid. The energy spectrum of radiation may be estimated by performing arithmetic processing on the count value of each pixel 201. The direction and the distance of the irradiating unit 101 may be estimated from the count values of the plurality of pixels 201. Further, the composition and the physical property value of a substance may be calculated from the number of radiation photons of each energy that transmits through the object and a linear attenuation coefficient in each energy. For example, a process of calculating the effective atomic number of the object may be performed. For example, a process of correcting beam hardening may also be performed in which the relatively larger number of radiation photons having high energy enter as the object becomes thicker.

A radiation imaging apparatus (radiation imaging system) according to a second embodiment of the present invention will be described. Although pileup detection according to the aforementioned first embodiment use the processing unit 330 arranged in each pixel 201, these functions can be implemented by, for example, a program or software in the processor 103. That is, each pixel 201 can be formed by a circuit to output a signal corresponding to the light converted by the scintillator 105 and the detection count of the pileup and the output count of the detection signal can be obtained outside each pixel 201.

FIG. 10 is a view showing an equivalent circuit of a pixel in a sensor panel 106 according to this embodiment. A pixel 40 in the sensor panel 106 of this embodiment can include photoelectric conversion elements 401 and an output circuit unit 402. The photoelectric conversion elements 401 can typically be photodiodes. The output circuit unit 402 can include an amplification circuit unit 404, a clamp circuit unit 405, a sample and hold circuit unit 407, and a selection circuit unit 408.

Each photoelectric conversion element 401 includes a charge accumulation portion connected to the gate of a MOS transistor 404a of the amplification circuit unit 404. The source of the MOS transistor 404a is connected to a current source 404c via a MOS transistor 404b. The MOS transistor 404a and the current source 404c form a source follower circuit. The MOS transistor 404b is an enable switch which is turned on to set the source follower circuit in an operation state when an enable signal EN supplied to its gate is set at an active level.

In an example shown in FIG. 10, the charge accumulation portion of each photoelectric conversion element 401 and the gate of the MOS transistor 404a form a common node, and this node functions as a charge-voltage conversion unit that converts charges accumulated in the charge accumulation portion into a voltage. That is, a voltage V (=Q/C) determined by charges Q accumulated in the charge accumulation portion and a capacitance value C of the charge-voltage conversion unit appears in the charge-voltage conversion unit. The charge-voltage conversion unit is connected to a reset potential Vres via a reset switch 403. When a reset signal PRES is set at the active level, the reset switch 403 is turned on, and the potential of the charge-voltage conversion unit is reset to the reset potential Vres.

A clamp circuit unit 406 clamps, using a clamp capacitor 406a, noise output by the amplification circuit unit 404 in accordance with the reset potential of the charge-voltage conversion unit. That is, the clamp circuit unit 406 is a circuit configured to cancel this noise from a signal output from the source follower circuit in accordance with charges generated by photoelectric conversion in each photoelectric conversion element 401. This noise can contain kTC noise at the time of reset. Clamping is performed by setting a clamp signal PCL at the active level to set a MOS transistor 406b in an ON state, and then setting the clamp signal PCL at an inactive level to set the MOS transistor 406b in an OFF state. The output side of the clamp capacitor 406a is connected to the gate of a MOS transistor 406c. The source of the MOS transistor 406c is connected to a current source 406e via a MOS transistor 406d. The MOS transistor 406c and the current source 406e form a source follower circuit. The MOS transistor 406d is an enable switch which is turned on to set the source follower circuit in the operation state when an enable signal EN0 supplied to its gate is set at the active level.

A signal output from the clamp circuit unit 406 in accordance with the charges generated by photoelectric conversion in each photoelectric conversion element 401 is written, as an optical signal, in a capacitor 407Sb via a switch 407Sa by setting an optical signal sampling signal TS at the active level. A signal output from the clamp circuit unit 406 when the MOS transistor 406b is set in the ON state immediately after the potential of the charge-voltage conversion unit is reset is a clamp voltage. This noise signal is written in a capacitor 407Nb via a switch 407Na by setting a noise sampling signal TN at the active level. This noise signal includes the offset component of the clamp circuit unit 406. The switch 407Sa and the capacitor 407Sb form a signal sample and hold circuit 407S. The switch 407Na and the capacitor 407Nb form a noise sample and hold circuit 407N. The sample and hold circuit unit 407 includes the signal sample and hold circuit 407S and the noise sample and hold circuit 407N.

When a driving circuit unit 41 drives a row selection signal VST at the active level, a signal (optical signal) held in the capacitor 407Sb is output to a signal line 45S via a MOS transistor 408Sa and a row selection switch 408Sb. At the same time, a signal (noise) held in the capacitor 407Nb is also output to a signal line 45N via a MOS transistor 408Na and a row selection switch 408Nb. The MOS transistor 408Sa forms a source follower circuit together with a constant current source (not shown) provided in the signal line 45S. Similarly, the MOS transistor 408Na forms a source follower circuit together with a constant current source (not shown) provided in the signal line 45N. The MOS transistor 408Sa, and the row selection switch 408Sb form a signal selection circuit unit 408S. The MOS transistor 408Na and the row selection switch 408Nb form a noise selection circuit unit 408N. The selection circuit unit 408 includes the signal selection circuit unit 408S and the noise selection circuit unit 408N.

The pixel 40 may include an addition switch 409S that adds optical signals of the plurality of adjacent pixels 40. In an addition mode, an addition mode signal ADD is set at the active level and the addition switch 409S is set in the ON state. Consequently, the addition switch 409S connects the capacitors 407Sb of the adjacent pixels with each other, averaging the optical signals. Similarly, the pixel 40 may include an addition switch 409N that adds noise of the plurality of adjacent pixels 40. When the addition switch 409N is set in the ON state, the addition switch 409N connects the capacitors 407Nb of the adjacent pixels with each other, averaging the noise. An addition unit 409 includes the addition switch 409S and the addition switch 409N.

The pixel 40 may include a sensitivity change unit 405 configured to change sensitivity. The pixel 40 can include, for example, a first sensitivity conversion switch 405a and a second sensitivity conversion switch 405a', and their accompanying circuit elements. When a first change signal WIDE is set at the active level, the first sensitivity conversion switch 405a is turned on, and the capacitance value of a first additional capacitance 405b is added to the capacitance value of the charge-voltage conversion unit. This decreases sensitivity of the pixel 40. When a second change signal WIDE2 is set at the active level, the second sensitivity conversion switch 405a' is turned on, and the capacitance value of a second additional capacitance 405b' is added to the capacitance value of the charge-voltage conversion unit. This further decreases sensitivity of the pixel 40. By adding a function of thus decreasing sensitivity of the pixel 40, it becomes possible to receive the larger amount of light and enlarge a dynamic range. When the first change signal WIDE is set at the active level, an enable signal ENw is set at the active level to cause a MOS transistor 404a', instead of the MOS transistor 404a, to perform a source follower operation.

The output from such an above-described pixel circuit is converted into a digital value by an A/D converter (not shown), and then supplied to a processor 103. Then, processes corresponding to the operations of a conversion unit 302, comparison units 303, memories 304, and detection units 307 are performed by software in the processor 103.

First, the processor 103 calculates a differential value of the output of the pixel circuit as the process corresponding to each conversion unit 302. Next, the processor 103 compares the calculated differential value with a digital value corresponding to each reference voltage 306 as the process corresponding to the corresponding comparison unit 303. The processor 103 outputs a digital value "1" if the differential value is equal to or more than the digital value corresponding to each reference voltage 306 and outputs a digital value "0" if the differential value is less than the digital value corresponding to each reference voltage 306. Then, as the process corresponding to each detection unit 307 and each memory 304, a digital value corresponding to a signal pattern 309 output by the process corresponding to each comparison unit 303 is compared with a digital value corresponding to each determination criterion 308, detecting pileup. Whether to obtain the detection count of light by the pixel is decided in accordance with whether pileup is detected. As in the first embodiment, the signal pattern 309 is, for example, a multi-bit digital value formed from the output of the process corresponding to each comparison unit 303 between the pixel that outputs the detection signal indicating that light is detected, and one or more pixels that output the detection signals in the same period and is continuous from the pixel. Then, the processor 103 generates an image based on the count. These processes can be executed, for example, by the CPU of the processor 103. The storage region that stores the detection count is allocated in the memory of the processor 103. As in the first embodiment, a plurality of digital values corresponding to the determination criteria 308, processes corresponding to the detection units 307, and storage regions corresponding to the memories 304 may exist. The same also applies to another collation processing or operation.

The functions of a processing unit 330 including the voltage conversion unit 302, the comparison units 303, the memories 304, and the detection units 307 according to the present invention can be arranged in each pixel 201 of the sensor panel 106 as in the first embodiment. Alternatively, all the processes can be performed by software as in the second embodiment. However, the present invention is not limited to these embodiments. At least some of the processes, such as the voltage conversion unit 302 and the comparison units 303, performed in the processing unit 330 can be arranged in each pixel 201 of the sensor panel 106 and the remaining processes corresponding to the memories 304 and the detection units 307 can be performed by software. Furthermore, the functions can be performed not by software but by a circuit provided outside the sensor panel 106 in this case, the circuit may be formed by, for example, FPGA.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage distributed computing systems, an optical disk (such as a compact disc (CD), digital versatile disc (DVD), or Blu-ray Disc (BD)™), a flash memory device, a memory card, and the like.

While the present has been described with to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-139104, filed Jul. 10, 2015 which is hereby incorporated by reference wherein in its entirety.

The invention claimed is:

1. A radiation imaging apparatus comprising:
a scintillator configured to convert radiation into light; a sensor panel in which a plurality of pixels each comprising a light detector configured to detect the light is arranged in a two-dimensional array; and a processing unit,
wherein the processing unit comprises
a signal generating unit configured to output signals indicating intensities of the light detected by the light detector of each of the plurality of pixels, and
a detection unit configured to identify a group of pixels each of which outputs a signal of a level exceeding a reference value out of the signals and detect, based on a pattern of the group, pileup in which a plurality of radiation photons is detected as a single radiation photon.

2. The apparatus according to claim 1, wherein the pixels that form the group output detection signals each indicating that light is detected out of the signal in the same period, and are formed by one pixel of interest and not less than one pixel continuous from the pixel of interest, and
the detection unit detects pileup from the group by determining whether at least one of the number of pixels that form the group, an arrangement of the pixels that form the group, and a level of the detection signal output from each of the groups satisfies not less than one determination criterion indicating pileup.

3. The apparatus according to claim 2, wherein the not less than one determination criterion includes a case in which the number of pixels that form the group is larger than a predetermined number.

4. The apparatus according to claim 2, wherein the not less than one determination criterion includes a case in which the detection signal, out of the detection signals output from the group, which indicates that an intensity of light is higher than a predetermined level, is output.

5. The apparatus according to claim 2, wherein the detection signal has a plurality of levels according to the intensities of the light detected by the light detectors, and
the not less than one determination criterion includes a case in which the number of pixels each outputting the detection signal indicating the highest-level intensity of the light out of the detection signals output from the group is larger than a predetermined number.

6. The apparatus according to claim 2, wherein the detection signal has the plurality of levels according to the intensities of the light detected by the light detectors, and
the not less than one determination criterion includes a case in which the level of the detection signal output from the group has not less than two peaks in the arrangement of the pixels that form the group.

7. The apparatus according to claim 2, wherein the not less than one determination criterion includes a case in which the number of pixels for one of each row and each column increases after a decrease in one of a column direction and a row direction in the arrangement of the pixels that form the group.

8. The apparatus according to claim 2, wherein the not less than one determination criterion is a plurality of determination criteria, and
the detection unit detects pileup by determining whether the group satisfies the plurality of determination criteria.

9. The apparatus according to claim 8, wherein the detection unit detects pileup if the group satisfies at least one determination criterion out of the plurality of determination criteria.

10. The apparatus according to claim 2, wherein if the number of the pixels that form the group is smaller than a predetermined number, the detection unit does not perform a determination for detecting pileup.

11. The apparatus according to claim 2, wherein in order to generate a captured image, the processing unit
increments a count of the number of times each pixel that forms the group outputs the detection signal if pileup is not detected from the group, and
does not increment a count of the number of times each pixel that forms the group outputs the detection signal if pileup is detected from the group.

12. The apparatus according to claim 11, wherein the processing unit comprises, in each of the plurality of pixels, a memory configured to store an output count of the detection signal.

13. The apparatus according to claim 2, wherein in order to generate a captured image, the processing unit
increments a count of the number of times each pixel that forms the group outputs the detection signal if pileup is not detected from the group, and
if pileup is detected from the group,
converts the group caused by a plurality of radiation photons into a plurality of groups caused by respective radiation photons and
increments a count of the number of times each pixel that forms the plurality of groups outputs the detection signal.

14. The apparatus according to claim 2, wherein in order to generate a captured image, the processing unit increments a count of the number of times the pixel of interest outputs the detection signal if the detection signal is not detected in a pixel adjacent to the pixel of interest.

15. The apparatus according to claim 1, wherein the signal generating unit comprises voltage conversion units configured to convert signals output from the light detectors into voltage signals, and comparison units configured to compare voltages of the voltage signals with a reference voltage and generate comparison result signals indicating comparison results.

16. The apparatus according to claim 15, wherein the detection unit identifies a group of pixels that output signals each indicating that light is detected out of the comparison result signals in the same period, the group being formed by one pixel of interest and not less than one pixel continuous from the pixel of interest, and detects pileup based on a pattern of the group.

17. The apparatus according to claim 1, wherein at least part of the processing unit is arranged in each pixel of the plurality of pixels.

18. A control method of a radiation imaging apparatus that comprises a scintillator configured to convert radiation into light and a sensor panel in which a plurality of pixels each comprising a light detector configured to detect the light is arranged in a two-dimensional array, the method comprising:

outputting signals indicating intensities of the light detected by the light detectors of the plurality of pixels;

identifying a group of pixels each of which outputs a signal of a level exceeding a reference value out of the signals; and detecting, based on a pattern of the group, pileup in which a plurality of radiation photons is detected as a single radiation photon.

19. A non-transitory computer-readable storage medium storing a program for causing a computer to execute a control method of a radiation imaging apparatus that comprises a scintillator configured to convert radiation into light and a sensor panel in which a plurality of pixels each comprising a light detector configured to detect the light is arranged in a two-dimensional array, the method comprising:

outputting signals indicating intensities of the light detected by the light detectors of the plurality of pixels;

identifying a group of pixels each of which outputs a signal of a level exceeding a reference value out of the signals; and detecting, based on a pattern of the group, pileup in which a plurality of radiation photons is detected as a single radiation photon.

\* \* \* \* \*